United States Patent [19]

William

[11] Patent Number: 5,211,627
[45] Date of Patent: May 18, 1993

[54] CATHETER AND METHOD FOR INFUSION OF AERATED LIQUID

[75] Inventor: Howat L. William, Stoneham, Mass.

[73] Assignee: C. R. Bard, Inc., Murray Hill, N.J.

[21] Appl. No.: 654,355

[22] Filed: Feb. 12, 1991

[51] Int. Cl.⁵ ............................................ A61M 37/00
[52] U.S. Cl. ...................................... 604/82; 604/280
[58] Field of Search ................. 604/43, 45, 82, 83, 604/23, 24, 26, 191, 264, 280; 128/656-658

[56] References Cited

U.S. PATENT DOCUMENTS

| | | | |
|---|---|---|---|
| 2,112,160 | 3/1938 | Johnson | 604/82 X |
| 3,470,869 | 10/1969 | Fenton et al. | 128/658 |
| 3,828,980 | 8/1974 | Creighton et al. | |
| 3,968,796 | 7/1976 | Baker | 604/24 X |
| 4,040,420 | 8/1977 | Speer | 604/82 |
| 4,260,077 | 4/1981 | Schroeder | |
| 4,265,251 | 5/1981 | Tickner | 128/660.02 |
| 4,318,402 | 3/1982 | Vaillancourt | |
| 4,405,313 | 9/1983 | Sisley et al. | |
| 4,442,843 | 4/1984 | Rasor et al. | |
| 4,568,329 | 2/1986 | Mahurkar | |
| 4,583,968 | 4/1986 | Mahurkar | |
| 4,610,666 | 9/1986 | Pizzino | 604/191 |
| 4,631,055 | 12/1986 | Redl et al. | 604/82 |
| 4,676,778 | 6/1987 | Nelson, Jr. | 604/45 |
| 4,692,141 | 9/1987 | Mahurkar | |
| 4,805,628 | 2/1989 | Fry et al. | |
| 4,807,625 | 2/1989 | Singleton | 128/361 |
| 4,808,155 | 2/1989 | Mahurkar | |
| 4,846,405 | 7/1989 | Zimmermann | 239/422 |
| 4,863,716 | 9/1989 | Quay et al. | |
| 4,874,368 | 10/1989 | Miller et al. | 604/82 |
| 4,978,336 | 12/1990 | Capozzi et al. | 604/82 |
| 5,015,232 | 5/1991 | Maglinte | 604/96 |
| 5,024,615 | 6/1991 | Büchel | 604/119 |
| 5,029,580 | 7/1991 | Radford et al. | 128/207.14 |

FOREIGN PATENT DOCUMENTS 1323082  7/1987  U.S.S.R.

OTHER PUBLICATIONS

"The Lancet", *New Inventions*, Oct. 29, 1955, p. 908.
Article: "Fallopian Tubal Patency Assessed by Ultrasound Following Fluid Injection", by Richman, et al. *Radiology* 1984; 152(2): 507-510.

*Primary Examiner*—John D. Yasko
*Assistant Examiner*—Adam J. Cermak
*Attorney, Agent, or Firm*—Darby and Darby

[57] ABSTRACT

A catheter having a lumen for delivering air and a lumen for delivering fluid, such as water. Each lumen extends from the proximal end to the distal end of the catheter. An opening is formed between the air and fluid lumens adjacent the distal end to allow communication between the lumens to allow mixing of the air and fluid. A syringe having a fluid barrel and an air barrel is connected to the catheter to communicate with the respective fluid and air lumens.

7 Claims, 1 Drawing Sheet

FIG. 1
FIG. 2
FIG. 3
FIG. 4

CATHETER AND METHOD FOR INFUSION OF AERATED LIQUID

BACKGROUND OF THE INVENTION

1. Field of the Invention

This invention relates to a catheter for use in introducing an aerated stream of liquid into a body cavity. More specifically, this invention relates to a catheter of particular utility in ultrasonic hysterosalpingography.

2. Description of the Related Art

The use of air bubbles as an echogenic medium is known. A liquid is temporarily aerated by shaking vigorously. The aerated liquid is introduced through a catheter into a cavity in the body to enhance the ultrasound opacity of the cavity. The aerated liquid is subsequently visualized with ultrasound, transiently outlining the cavity into which it is injected.

Heretofore, the aerated solution, i.e., the mixture of air and water, was made at the proximal end of the catheter or in a syringe inserted into the proximal end of the catheter. Thus, the aerated solution had to travel the length of the catheter to the distal end portion for delivery into the cavity. This resulted in the bubbles coalescing and/or dissolving by the time they reached the cavity. Consequently, this technique did not enable a steady stream of small bubbles to be consistently produced, thereby inhibiting ultrasound induced visualization of the cavity.

Moreover, the prior art method of introducing aerated solutions at the proximal end was limited in that controlled stopping and starting could not be achieved since the solution was injected from a position remote from the distal end. Thus, placement of small, controllable amounts of air bubbles at specific locations could not be obtained effectively.

To one application in which an aerated solutions may be used for ultrasound visualization is hysterosalpingography (HSG), a diagnostic procedure for analyzing the uterus and fallopian tubes to determine if they are complete or if there are any blockages which are causing infertility. Hysterosalpingography is commonly performed by injecting radiopaque dye into the fallopian tube and then using fluoroscopic examination for visualization. However, this exposes the patient to ionizing radiation which might detrimentally effect the patient's health. Additionally, it increases the cost of the procedure because a radiologist is required.

Accordingly, a principal object of the invention is to provide a catheter construction capable of infusing an aerated stream of liquid into a body cavity for ultrasonic visualization, particularly for hysterosalpingography.

A more specific object of the invention is to provide a catheter capable of delivering an aerated stream of liquid to a body cavity wherein the tendency of the bubbles to coalesce and/or dissolve before reaching the region to be visualized is substantially reduced.

SUMMARY OF THE INVENTION

The present invention overcomes the problems and deficiencies of the prior art by providing a catheter comprising a tubular element having a first lumen for delivering air and a second lumen for delivering fluid. The lumens are disposed parallel to one another and extend longitudinally from the proximal end portion to the distal end portion of the tubular element. The proximal end of the two lumens are open and separate. An orifice is formed between the first and second lumens in the distal end portion to provide communication between the lumens to allow mixing of air and fluid. The orifice for mixing the air and fluid, being located at the distal end portion, reduces the prior art problems of bubbles coalescing and/or dissolving as the aerated liquid travels along the length of the catheter to the cavity.

The invention may also include a double-barreled syringe connected to the catheter. The second barrel has an internal diameter and length greater than the internal diameter and length of the first barrel. The larger barrel is for delivering fluid and the smaller barrel is for delivering air to the respective fluid and air lumens.

DESCRIPTION OF THE DRAWINGS

The objects, features, and advantages of the present invention will be more fully appreciated as the same becomes better understood from the following detailed description of the present invention, when considered in connection with the accompanying drawings, in which:

FIG. 1 is a side view of the catheter of the present invention, and also showing the syringe in block diagram;

FIG. 2 is an enlarged longitudinal section view of the distal end portion of the catheter;

FIG. 3 is a cross-section view taken along lines 3—3 of FIG. 2; and

FIG. 4 is a cross-section view of an alternate embodiment of the distal end portion of the catheter.

DETAILED DESCRIPTION OF THE PREFERRED EMBODIMENTS

Figures 1, 2, 3, 4:
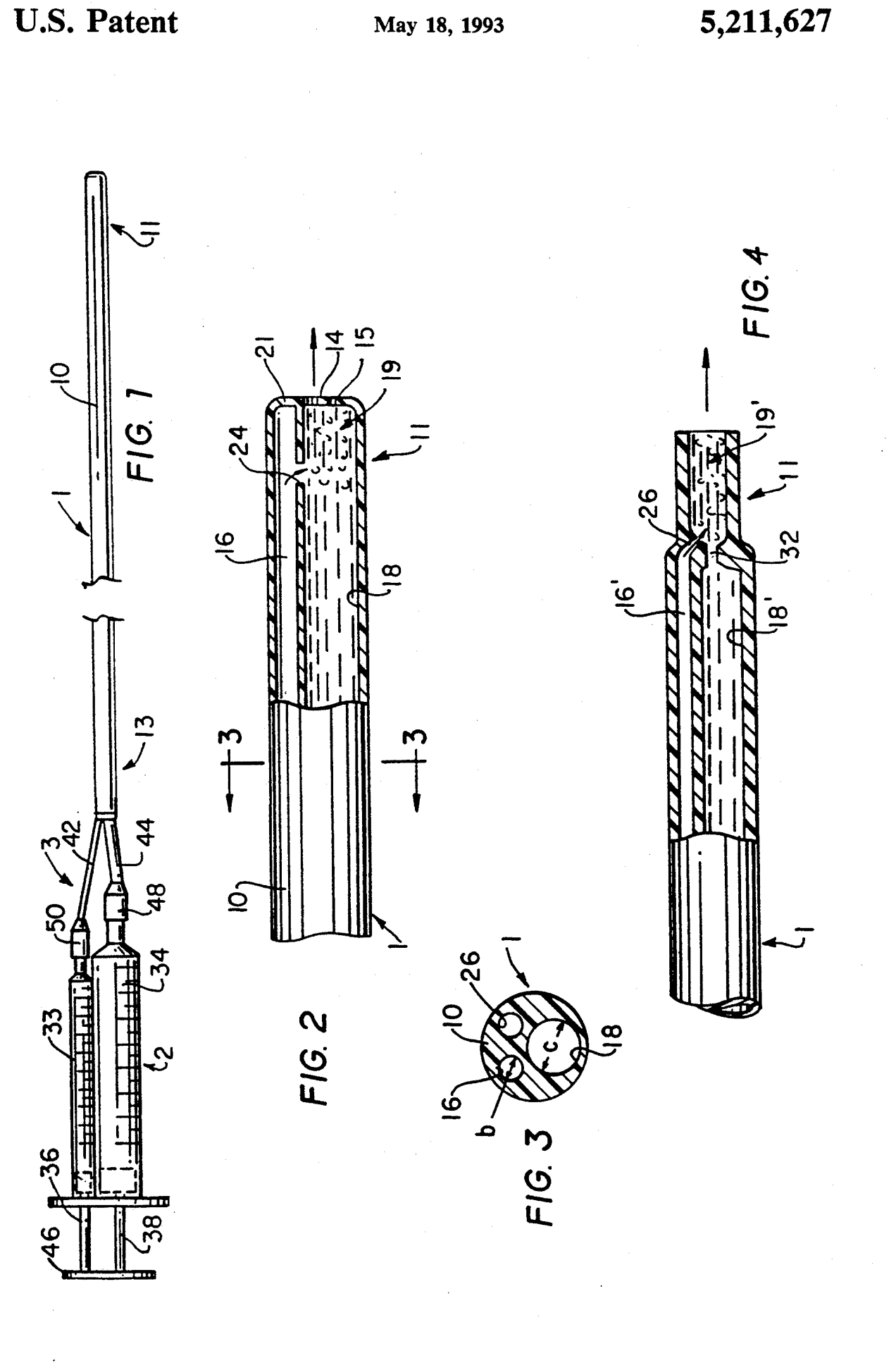

Referring now to the drawings, wherein like reference numerals represent identical or corresponding parts throughout the several views, FIG. 1 illustrates a syringe 2 connected to a catheter 1 by a bifurcated fitting 3.

Catheter 1 of the present invention includes an elongated, cylindrical tubular element 10 having a distal end portion 11 adapted to be inserted into the patient and a proximal end portion 13 remote from the distal end portion 11. Tubular element 10 is preferably extruded from a thermoplastic material such as urethane, although other materials can be utilized.

As shown in FIGS. 2 and 3, an air lumen 16 for delivering air is formed within the tubular element 10, extending longitudinally through its entire length from the proximal end portion 13 to the distal end portion 11. The distal end of air lumen 16 is closed as designated by reference numeral 21. The proximal end of air lumen 16 is open.

A liquid lumen 18 for delivering liquid such as water is formed within tubular element 10, spaced apart and parallel to air lumen 16, also extending longitudinally through the entire length of tubular element 10. The proximal end of lumen 18 is open, and an aperture 14 is formed in its distal end 15.

In the embodiment shown in FIG. 2, an orifice 24 is formed between the air and fluid lumens 16 and 18 at the distal end portion 11, preferably slightly rearwardly of the distal end or tip 17 of the tubular element 10. This causes air from lumen 16 to be mixed with the water in lumen 18 in a distal diffusing zone 19 within lumen 18. In an alternate embodiment shown in FIG. 4, the distal end of air lumen 16' terminates in an orifice 26 so that the air from air lumen 16' is mixed with the fluid from fluid lumen 18' in diffusing zone 19' of tubular element 10'. Fluid lumen 18' includes a restricted portion 32 to provide low pressure, high velocity fluid flow.

In both embodiments, the orifice between the lumens is formed in the distal end portion 11. Thus, the air and fluid can be mixed in-vivo to produce microbubbles near or at the site which is to be scanned ultrasonically. This reduces the coalescing or dissolving of bubbles which would otherwise occur if the aerated solution were mixed at the proximal end portion and had to travel the entire length of the catheter.

The important factor in determining the size of the microbubbles in the liquid is the difference in pressure in the air and water lumens and the size of the orifice between the two lumens. As explained below, this pressure differential may be determined by the relative diameter of the syringes used to inject the air and water. While the diameters of the lumens 16 and 18 is not critical, air lumen 16 preferably has a diameter b smaller than the diameter c of the fluid lumen 18 for transport of a smaller volume of air with respect to the volume of fluid. In a preferred embodiment, the diameter of the air lumen ranges from 0.014 to 0.016 inches and the diameter of the fluid lumen ranges from 0.035 to 0.037 inches, depending in part on the size of tubular element 10. The diameter of orifice 24 (or 26) may be from 0.003 inches to 0.016 inches.

A longitudinal wire lumen 26 (FIG. 3) to receive a reinforcing wire (not shown) is formed within tubular element 10, extending from the distal end portion 11 to proximal end portion 13 and parallel to air and fluid lumens 16 and 18. The wire serves to increase rigidity of the tubular element 10.

In a preferred embodiment, a single syringe is used to infuse the air and fluid simultaneously into the lumens 16 and 18, respectively. As shown in FIG. 1, syringe 30 includes an air barrel 33 and a liquid barrel 34. Each barrel is provided with a conventional plunger 36 and 38, respectively. Plungers 36 and 38 are joined at their proximal ends by a finger grip 46 so that the plungers 36 and 38 are operated simultaneously. Plungers 36 and 38 function in conventional fashion to expel the air and water in the barrels or to draw fluid into the barrels when the plungers are retracted.

As shown in FIG. 1, the liquid barrel 34 is larger than the air barrel 33 so that the volume of air infused into the catheter is less than the volume of water for any given stroke. The amount of air and water infused through the catheter is, of course, controlled by the volume of the respective barrels 33 and 34. As indicated above, the size of the bubbles formed in the infusion area 19 (19') is determined in part by the pressure applied to the air and water. It is preferred that the diameter of the air barrel 33 be less than the diameter of the water barrel 34 so that the pressure in the air lumen is higher than the liquid pressure. In one embodiment, successful results have been achieved with the following dimensions:

inner diameter of barrel 33:0.191 inches
inner diameter of barrel 34:0.570 inches
volume of barrel 33:1 cc
volume of barrel 34.:10 cc As shown in FIG. 1, the distal end of liquid barrel 34 extends slightly beyond the distal end of the air barrel 33. This allows the syringe to be placed in water for refilling without causing the water to be drawn into the air barrel 33. By withdrawing the plungers 36 and 38 simultaneously with only the distal end of barrel 34 immersed in water, the barrel 34 is filled with water and the barrel 33 simultaneously filled with air.

The lumens 16 and 18 of catheter 1 may be connected to syringe 2 in any appropriate fashion. For example, flexible tubes 42 and 44 may be attached by adhesive means to the proximal ends of the lumens 16 and 18, respectively. The tubes 42 and 44 may terminate in fittings 50 and 48 which are adapted to tightly receive the distal ends of the barrels 33 and 34. Conventional luer fittings may also be used.

As indicated above, the principal use for the catheter is hysterosalpingography. In a such a procedure, the doctor inserts the distal end of the catheter into the patient's uterus, for example, in a position to infuse the water into the Fallopian tubes to determine whether they are complete or if there are any blockages. When the catheter is in place, the doctor exerts a pressure on the finger grip 46 of syringe 2 causing the plungers 36 and 38 to simultaneously expel air and water into the lumens 16 and 18, respectively, of catheter 1. The air within the lumen 16 which is under relatively high pressure exits through the orifice 24 and mixes vigorously with the water within the diffusing zone 19 of the lumen 18 (in FIG. 2). This action causes the formation of a multiplicity of microbubbles within the stream of water thereby aerating the water stream which is immediately expelled through the opening 14 in the distal end of the catheter. Since the end of the catheter is in proximity to the region of the uterus which is to be visualized ultrasonically, the microbubbles formed in the distal end of the catheter will not tend to coalesce or dissolve before serving as an ecogenic medium for the ultrasonic energy which is propagated into the region of interest by the diagnostic equipment. The aerated fluid thereby serves as an effective sonographic contrast medium which permits the diagnostic procedure to determine tubular patency.

The procedure is essentially the same with the embodiment shown in FIG. 4 wherein the water and air from the lumens 18' and 16' are mixed in a diffusing zone 19' in the distal end of the catheter 1. As mentioned above, the size of the microbubbles within the water stream emitted from the catheter is a function of the relative pressure of the air and water in lumens 16 and 18, respectively, and the size of the orifice 24. These values can be determined empirically to provide the desired results in the diagnostic procedure.

In operation, the grip 46 of syringe 2 is pressed forwardly to simultaneously inject air through air barrel 33 into lumen 16 and water through liquid barrel 34 into lumen 18. In the embodiment of FIG. 2, the air travels through orifice 24, in the lumen 18. This aerates the water in zone 19 which exits through aperture 14 in distal tip 15 of fluid lumen 18 into the body cavity. In the embodiment of FIG. 5, air travels through opening 26 in the direction of arrow E where it mixes with the fluid in area 19. The aerated solution exits through the distal end of tubular element 10, flowing into the cavity in the direction of arrow F. The introduction of aerated fluid into the body allows clear visualization utilizing ultrasound.

It will be understood that the foregoing is considered as illustrative only of the principles of the invention. Therefore, within the scope of the appended claims, the invention may be practiced otherwise then as specifically described herein.

What is claimed is:

1. Apparatus for injecting an aerated stream of liquid into a body cavity, comprising:
   a catheter having a distal end portion for insertion into a body cavity, a proximal end portion remote from said distal end portion, first and second lumens extending from said proximal end portion to said distal end portion, and an opening formed at said distal end portion between said first and second lumens to provide communication therebetween; and
   a syringe connected to said proximal end of said catheter, said syringe having first and second barrels communicating with said respective first and second lumens, and first and second plungers mechanically linked together and situated in said first and second barrels for simultaneously infusing air and liquid into said first and second lumens, respectively.

2. An apparatus as recited in claim 1, wherein said first lumen is for receiving and delivering air from said first barrel and said second lumen is for receiving and delivering water from said second barrel.

3. A catheter as recited in claim 2, wherein the internal diameter of said second barrel is greater than the internal diameter of said first barrel.

4. A catheter as recited in claim 2, wherein the volume of said second barrel is greater than the volume of said first barrel.

5. A catheter as recited in claim 4, wherein the length of said second barrel is greater than the length of said first barrel.

6. A catheter as recited in claim 2, further comprising a plunger attached to said proximal end of the syringe for simultaneously purging said first and second barrels.

7. A method of aerating a liquid in an ultrasonic diagnostic procedure comprising the steps of injecting air and liquid through separate lumens of a catheter, mixing the air and liquid at a distal end portion of the catheter, and injecting the aerated liquid through the catheter into a body cavity.

* * * * *

UNITED STATES PATENT AND TRADEMARK OFFICE
CERTIFICATE OF CORRECTION

PATENT NO. : 5,211,627
DATED : May 18, 1993
INVENTOR(S) : William L. Howat

It is certified that error appears in the above-indentified patent and that said Letters Patent is hereby corrected as shown below:

On the cover page , Item ]75] Inventors: delete "Howat L. William" substitute therefor --William L. Howat, --.

Signed and Sealed this

Eighteenth Day of July, 1995

Attest:

BRUCE LEHMAN

Attesting Officer     Commissioner of Patents and Trademarks